United States Patent [19]

Huber

[11] Patent Number: 6,143,753
[45] Date of Patent: Nov. 7, 2000

[54] PHARMACEUTICAL COMPOSITION FOR THE TREATMENT OF MALIGNANT NEOPLASMS AND IMMUNOSUPPRESSIVE DEFICIENCIES AND ITS METHOD OF PRODUCTION

[76] Inventor: Paul Huber, Fazenda Holambra D, Caxal Postal n° 400, Rodovia Raposo Tavares Km 256 18725-000, Paranapanema, Brazil

[21] Appl. No.: 09/202,126
[22] PCT Filed: Jun. 29, 1998
[86] PCT No.: PCT/BR98/00045
    § 371 Date: Mar. 1, 1999
    § 102(e) Date: Mar. 1, 1999
[87] PCT Pub. No.: WO99/01125
    PCT Pub. Date: Jan. 14, 1999

[30] Foreign Application Priority Data

Jul. 2, 1997 [BR] Brazil ................................. 9702557 U

[51] Int. Cl.[7] ........................ A01N 43/54; A61K 31/515
[52] U.S. Cl. ............................................ 514/274; 514/416
[58] Field of Search ...................... 514/274, 416

[56] References Cited

PUBLICATIONS

Kruglyakova et al., "Investigation of the effect of UV light of varying wavelength on DNA with different protein content in the presence of endogenous sensitizers", Stud. Biophys. 85(1), 55–56, 1981.

Tarui et al., "Thermodynamic effect of complementary hydrogen bond base paring on aromatic stacking interaction in the guanine–X–Trp complex (X=adenosin, guanine, ctosine, thymine)", Chem. Pharm. Bull., 44(11), 1998–2002, 1996.

Koshima et al, "Photochemical behavior of crystals and mixed crystals composed of nucleic acid bases", Photomed. Photobiol. 17, 109–110, 1995.

Primary Examiner—Dwayne C. Jones
Attorney, Agent, or Firm—Adelman, Frayne & Schwab

[57] ABSTRACT

A pharmaceutical composition for the treatment of malignant neoplasms and immunosuppressive deficiencies and its method of production, the active ingredients of said composition being DL-kinurenine associated with thymine.

10 Claims, No Drawings

PHARMACEUTICAL COMPOSITION FOR THE TREATMENT OF MALIGNANT NEOPLASMS AND IMMUNOSUPPRESSIVE DEFICIENCIES AND ITS METHOD OF PRODUCTION

This application is a 371 of PCT/BR 98/00045 which has a filing date of Jun. 29, 1998.

FIELD OF THE INVENTION

The present invention refers to a pharmaceutical composition for the treatment of malignant neoplasms and immunosuppressive deficiencies, by re-establishing the biochemical balance within the cells, mainly those cells undergoing a disordered reproduction, and to a method for producing said pharmaceutical composition.

BACKGROUND OF THE INVENTION

Nowadays, the existence of several types of cancer control by means of conventional treatments has conducted, after studies based on cellular biochemistry, to the provision of a pharmaceutical composition formed by an essential aminoacid of the benzoic genesis and by a genetic derivative of a pyrimidinic nitrogenized base. The experiment has clinically proved its efficiency on the neoplastic cells, avoiding their disordered reproduction.

DISCLOSURE OF THE INVENTION

Thus, it is a first objective of the present invention to use the efficiency of the active ingredients of an essential aminoacid of the benzoic genesis with a pyrimidinic nitrogenized base in a biologically acceptable pharmaceutical formula in the following compositions: DL-kinurenine, [2-amine-3-(2-aminebenzene)propionic acid] and tymine, [2,1 dihydroxy-5-methyl-pyrimidine;5-methyluracil].

A further objective of the present invention is to provide a method for producing a pharmaceutical composition, which is formulated for the dissolution of 1.5–6.0 grams, preferably 3–4 grams of DL-kinurenine and 1.2–7.0 grams, preferably 2.5–3.5 grams of tymine in 50 ml of distilled water, preferably at about 50° C., resulting in a stabilized solution with a neutral pH of about 5.6 to 9.0, preferably from 6.8 to 7.3 by adding an adequate amount of potassium or sodium hydroxide.

Taking into account that DL-kinurenine is the final product of anthranil transformation in the biochemical reactions, in which is included tryptophan, which precedes kinurenine, it has been verified that it is possible to substitute kinurenine by tryptophan in the desired pharmaceutical composition, without modifying the effects. Tryptophan [(R)-2-amine-3-(indole-propionic acid) associated with tymine has become viable for the pharmaceutical composition in the originally suggested proportions.

The substances mentioned in the described pharmaceutical composition have their active ingredients diluted in distilled water or in the form of encapsulated powder and are intended for oral administration. They result in a new drug for treating the biochemical disorders found in all neoplastic cells and with immunosuppressive deficiencies.

The observation of the biochemical reactions that occur within the cells, in terms of DNA and RNA, between the aminoacids and the functions of the nitrogenized bases in the presence of the enzymatic systems, has allowed the correction of several forms of lesions in the chromossomal structures caused by hydrolysis or external mutagenic agents, deaminating agents and alkylating agents (Ames, 1979, 204:587–593; Cairns, 1975,233:64–78; and Goodman and Gilman, 1987). It has been developed a pharmaceutical formulation, obtaining a product formed by the association of an aminoacid of the benzoic genesis with a pyrimidinic nitrogenized base which, inside the cell, in terms of DNA and RNA in the presence of carboxylase, produces a double effect, i.e., neutralizes the formylic radicals which appear during the irregular mitosis of the chromosomal structures and eliminates the energy produced with oxygen release for the formation of the neoplastic cells.

This process, called catacholase, stops the liberation of energy by oxygen and completes the neutralization of the formylic radicals, re-establishing the bridge with the deoxyribonucleoside of the DNA chromosomes (Lawitscka, Dados Informativos de Pesquisa (Research Informative Data), 1960). The neoplastic cells during the cellular mitosis have a defect in the ribonucleosidase of the purines. Failure in this purine formation makes the cell become cancerous.

Knowing that the nucleic acids are informative molecules which control the basic processes of the cellular metabolism, the synthesis of the macromolecules, the cellular differentiation and the transmission of the genetic inheritance, this new product has been induced to act directly in the interior of the cell (Valeriote and Santelli, 1984, 107–132).

The present product is found in both powder and liquid forms. As a powder, it is encapsulated with an innocuous vehicle, while in the liquid form it is an aqueous solution stabilized with a neutral pH.

The product consists essentially of DL-kinurenine aminoacid associated with the pyrimidinic nitrogenized base, tymine, and may be produced as a powder or liquid pharmaceutical formulation.

The maximum dose which is recommended to obtain the desired effect over the neoplastic cells is 275 mg/day of DL-kinurenine and 250 mg/day of tymine, in a pharmaceutical formulation which is orally administered each 8 hours, the serous level being maintained with no toxicity of the active ingredients of the components. Efficiency in a treatment of malignant neoplasms is achieved with the recommended dose of 100–1,500 mg/day of DL-kinurenine and 100–1,400 mg/day of tymine.

The product in question is indicated for malignant neoplasms and immunosuppressive deficiencies as a cellular restorer. It may be added in powder form to a nutritional supplement, when indicated in the diets of patients convalescing from surgeries of cancerous tumor removal and in the immunological deficiencies. It is innocuous, does not have contraindications and does not cause side effects and adverse reactions when properly used. The validity period is 24 months from the manufacture date, in which period no alterations were detected in the physical-chemical characteristics of its active ingredients. Either in capsules or in the liquid form, the product should be kept away from light, heat and humidity and packaged in a plastic container for the capsules or sachets, or in a dark glass container when in the liquid form.

The pharmaceutical composition of the drug named tk-3 comprises the following components in the liquid form:

| | |
|---|---|
| DL-kinurenine | 3.3 g |
| tymine | 3.0 g |
| potassium hydroxide | 0.63 g |
| distilled water | 50 ml |

In encapsulated powder or in sachets:

| | |
|---|---|
| DL-kinurenine | 3.3 g |
| tymine | 3.0 g |
| kaolin | 187 g |

For the total amount of 250 mg corresponding to capsules of 500 mg of the active ingredients of the substances.

In clinical experiments, based on studies and observations of the biochemical transformations of the active ingredient of the components of the pharmaceutical composition, it has been concluded that DL-kinurenine may be replaced by tryptophan in the same proportion, without altering the desired result for the treatment of patients with malignant neoplasms.

BEST MODE OF CARRYING OUT THE INVENTION

The knowledge of the chromosomal structures, DNA and RNA components, as well as the related biochemical reactions has permitted the detection of a defect in the ribonucleasidase of the purines. By using the essential aminoacid resulting from the transformation of anthranil, 2-benzoic aminoacid, into tryptophan and finally into DL-kinurenine, which is the third degree of the benzoic genesis of these aminoacids, associated with a pyrimidinic nitrogenized base, the tymine [2,4 dihydroxy-5-methylpyrimidine;5-methyluracil], it has been detected a cellular biochemical reaction taking place in the nucleosides and nucleotides of the neoplastic cells, by the enzymatic action of carboxylase. This biochemical reaction of the active ingredients of the product has the purpose of eliminating the energy produced by oxygen release and of neutralizing the nitrogen of the formylic radicals produced in the disordered cellular mitosis of the neoplastic cells. In this biochemical reaction of the cell, 5-methyluracil re-establishes the cellular genesis and DL-kinurenine eliminates the nitrogenized methylic and formylic radicals which appear during the cellular mitosis. 5-methyluracil re-establishes the bridge with the deoxyribonucleoside, with the atypical chromosomes being eliminated, since they do not obey the benzoic genesis of the cell (Lawitscka, Reseach Informative Data, 1960–1980); (Jones, 1980,49:253–279); Fraile, 1980, 2223–2228; Valeriote and Santelli, 1984, 107–132 and Jones, 1979,98:1–8).

The nucleotides and nucleosides of the normal cells take the cell to a mitosis, in which the chromosomes are multiplied in pairs and not as it occurs in the neoplastic cell, in which the multiplication takes place in groups of four.

The four purinic nitrogenized bases of DNA and RNA (Adenine and Guanine, A and G) and pyrimidinic bases of DNA (Citosine and Tymine, C and T) and of RNA (Citosine and Uracil, C and U), which are components of the nucleic acids, form together with glucose (pentose) the first link for the fusocellular mitosis, by action of ribonucleosidase, which effects the cellular mitotic genesis. A failure in this formation of the purines makes the cell become cancerous. A purine may be replaced by a ribonucleoside, but not in the cellular mitosis. In the mitosis it is irreplaceable. The oxyribonuclease and deoxyribonuclease enzymes are present in the mitotic cellular genesis, transformed by carboxylase. Deoxyribonuclease is the carrier of the cellular genesis and allows the communication among the chromosomes by means of 5-methyluracil, which eliminates the free oxygen by action of kinurenine over the formylic radicals, transforming in oxy-kinurenine formyl, neutralizing the energy of the cancerous cell. Once re-established the bridge with the deoxyribonucleoside by the transformation of uracil into 5-methyluracil- in the presence of tryptophan, transformed into oxykinurenine formyl, the formylic and methylic nitrogenized radicals are eliminated, allowing the cell to return to a normal mitosis (Lawitscka, Informative Data, 1960).

It may be observed that it is possible, by administering the product in its liquid or powder forms, to correct several forms of DNA lesions, which make the cell become cancerous.

Adults may take a recommended daily dose of 275 mg of DL-kinurenine or tryptophan and 250 mg/day of tymine. The daily dose of kinurenine may vary from 100 mg to 1,500 mg, the more indicated dose being 275 mg/day, as well as for tryptophan, and from 100 to 1,500 mg of tymine. These doses are recommended for both the liquid and powder forms. The normal serous level of tryptophan is 11+−2 mg/l and an adult excretes 50 mg of xanthurenic acid in the urine in 24 hours upon taking 2 g of tryptophan orally. Therefore, the indicated doses should not surpass the recommended limits. An overdose would cause pyridoxal deficiency and abnormal excretion of xanthurenic acid, resulting in pathological alterations, such as pyridoxine deficiency (vit. B6) and increase of urinary indoles (Hughes, Raine, 1966:399; Guibaut and Froelich, 1973, 112; Gehe=Mann, 1959, 1:165).

It should be noted that the present invention is not limited to the examples or details contained herein. The results described above, which have been obtained by using the present composition, confirm that this drug is adequate for the treatment of neoplasms and immunosuppressive deficiencies, the preparation of the composition being easily carried out with commercially available raw materials.

What is claimed is:

1. A method for producing a pharmaceutical composition for the treatment of malignant neoplasms and immunosuppressive deficiencies, which comprises the steps of dissolving about 1.2 to 7.0 grams of Thymine and about 1.5 to 6.0 grams of DL-Kinurenine in 50 ml of distilled water at a temperature of about 50° C., and adding a base selected from potassium hydroxide or sodium hydroxide, in order to obtain a stabilized solution with a pH from 6.5 to 9.0.

2. The method according to claim 1, wherein the pH is from 6.8 to 7.3.

3. The method as in claim 1 wherein about 2.5 to 3.5 grams of Thymine and about 3 to 4 grams of DL-Kinurenine are dissolved in 50 ml of distilled water at a temperature of about 50° C., and adding a base selected from potassium hydroxide or sodium hydroxide, in order to obtain a stabilized solution with a pH from 6.8 to 7.3.

4. The method according to claim 3 wherein DL-Kinurenine is substituted by Tryptophan.

5. A method for the treatment of malignant neoplasms and immunosuppressive deficiencies in humans, which comprises: administering to humans suffering from malignant neoplasms and immunosuppressive deficiencies a stabilized solution having a basic pH containing therapeutically effective amounts of Thymine and DL-Kinurenine.

6. The method of treatment of claim 5 wherein the solution has a pH of about 6.5 to 9.0 and contains from about 1.2 to 7.0 grams of Thymine and from about 1.5 to 6.0 grams of DL-Kinurenine in 50 ml of distilled water.

7. The method of treatment of claim 6 wherein the solution has a pH of about 6.8 to 7.3 and contains about 2.5 to 3.5 grams of Thymine and from about 3 to 4 grams of DL-Kinurenine in 50 ml of distilled water.

8. The method of treatment of claim 5 wherein Tryptophan is substituted for DL-Kinurenine.

9. The method of treatment of claim 6, wherein Tryptophan is substituted for DL-Kinurenine.

10. The method of treatment of claim 7, wherein Tryptophan is substituted for DL-Kinurenine.

* * * * *